United States Patent [19]

O'Brien et al.

[11] 4,115,435
[45] Sep. 19, 1978

[54] BISULFITE TERMINATED OLIGOMERS AS DISPERSING AGENTS

[75] Inventors: John T. O'Brien, Cheshire; Woodrow W. White, Oxford, both of Conn.

[73] Assignee: Uniroyal, Inc., New York, N.Y.

[21] Appl. No.: 726,034

[22] Filed: Sep. 23, 1976

Related U.S. Application Data

[63] Continuation-in-part of Ser. No. 493,382, Jul. 31, 1974, Pat. No. 4,004,939, which is a continuation-in-part of Ser. No. 456,397, Mar. 29, 1974, abandoned.

[51] Int. Cl.$^2$ .................. C07C 121/38; C07C 143/12; C07C 143/02
[52] U.S. Cl. ........................... 260/465.4; 260/513 R; 560/151
[58] Field of Search ............ 260/465.4, 481 R, 513 R; 560/151

[56] References Cited

U.S. PATENT DOCUMENTS

| 3,646,099 | 2/1972 | Dannals | 260/465.4 |
|---|---|---|---|
| 3,668,230 | 6/1972 | Dannals | 260/465.4 |
| 3,719,485 | 3/1973 | Ferro | 96/1.5 |
| 3,772,382 | 11/1973 | Dannals | 260/481 R |
| 3,839,405 | 10/1974 | Dannals | 260/481 R |
| 4,004,939 | 1/1977 | O'Brien et al. | 106/135 |

OTHER PUBLICATIONS

The Condensed Chem. Dictionary, 1966, pp. 911–912.

Primary Examiner—Joseph Paul Brust
Attorney, Agent, or Firm—Anthony Lagani, Jr.

[57] ABSTRACT

This invention relates to the use of bisulfite-terminated oligomers as dispersants for solid particulate matter, i.e., low molecular weight bisulfite-terminated polymers containing carboxylate groups and either cyano or carbomethoxy moieties are improved dispersants for solid particulate matter like pigments such as titanium dioxide, clay, calcium carbonate, talc, and zinc oxide, as well as for organic pigments. Particularly, these dispersants have been found useful for stabilizing paper coating compositions.

2 Claims, No Drawings

BISULFITE TERMINATED OLIGOMERS AS DISPERSING AGENTS

This application is a continuation-in-part of application Ser. No. 493,382, filed July 31, 1974 now U.S. Pat. No. 4,004,939, which is a continuation-in-part of application Ser. No. 456,397, filed Mar. 29, 1974 now abandoned.

This invention relates to the use of bisulfite-terminated oligomers as dispersing agents for the preparation of dispersions of inorganic and organic pigments, extenders, fillers, and other insoluble fine particles in aqueous systems. The other oligomers have been found especially useful as components of paper coating colors to stabilize slurries of deflocculated paper coating pigments. More specifically, oligomers represented by the following formula have been found to be so useful:

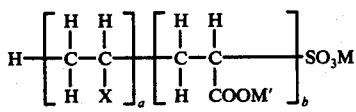

wherein M is an alkali metal or ammonium cation; X is selected from —CN and —COOCH$_3$; M' is a cation based on ammonia, an amine, or alkali metal; $a + b$ is from 4 to 150 and $a/a + b$ is from about 0 to not greater than 0.6.

The oligomers whose use as dispersants for solid particulate matter is claimed herein, are disclosed in U.S. Pat. No. 3,646,099 to L. E. Dannals. This patent discloses a general class of bisulfite-terminated oligomers prepared from a variety of monomers. This general glass of oligomers is stated to be useful as conductive agents and as surface active agents. However, it has been found that the specific oligomers useful for this invention are not surface active agents in that they have no effect on the surface tension of water as is demonstrated by example herein. Furthermore, it is well known to the art that the terms surface active agents and dispersing agents are not synonymous; they represent different facets of a similar problem.

Canadian Pat. No. 854,271 discloses fluid, aqueous clay dispersions containing sufficient polymeric polycarboxylate to disperse the clay, where the polycarboxylate dispersants are prepared from such as acrylic acid alone or acrylic acid and acrylamide copolymer or acrylonitrile and methacrylic acid copolymer. However, at no point is a bisulfite-terminated acrylic acid polymer nor is any acrylic acid-acrylonitrile copolymer disclosed.

Additionally, Japanese application No. 7,123,763 discloses an alkali metal salt of acrylic acid and methyl acrylate copolymer as a dispersing agent for paper pigments. However, the polymers do not have a bisulfite terminal group which is essential to the effectiveness of this invention. Japanese Pat. Nos. 7,136,883 and 7,233,055 disclose similar dispersing agents where the comonomer with acrylic acid is acrylamide and itaconic acid respectively. U.S. Pat. No. 3,594,203 discloses stable deflocculated aqueous clay slurries in which a soluble salt of a polyanionic organic polymer including sodium salt of carboxylated polyelectrolymer is employed to impart the stability. U.S. Pat. Nos. 3,736,165 and 3,737,333 discloses the use of the polyanionic organic polymer in wet processing of kaolin clay as a dispersant to deflocculate the clay.

The use of sodium polyacrylate as a deflocculant for paper coating pigments and a stabilizing agent in coating colors has been discussed further by M. E. Rohmann, *Wochenblatt fuer Papierfabrikation*, 3, 79 (1973).

A paper coating color comprises three basic components: a pigment dispersion, a pigment binder, and minor additives. The pigment such as kaolin or other clay, calcium carbonate, titanium dioxide, satin white, and barium sulfate or combinations thereof is dispersed in water using high speed dispersing equipment like a Cady Mill, Cowles Dissolver and Deliteur, or using a sigma blade mixer. Reagglomeration of the finely divided pigment particles is overcome by adding small amounts of certain dispersants including polyphosphates, naphthalenesulfonate-formaldehyde condensates or polyacrylate salts. The pigment binder may be natural or synthetic including such as casein, protein, starch, carboxylated SBR, polyvinyl acetate, polyvinyl alcohol, or vinyl acetate-acrylate copolymers. Minor additives include, besides the dispersant, crosslinking agents, optical brighteners, flow regulators, natural or synthetic thickeners, biocides, and defoamers or antifoams. Although the dispersant is a minor component in amount, it can have a pronounced effect on runability of the coating color and on the final properties of the coated sheet.

The preparation of high solids coating colors, which are essential to modern high speed coating processes, requires dispersion of high solids slurries of pigments. A dispersion of kaolin in water at 70% solids is a common slurry used in paper coating. While the polyphosphates including sodium hexametaphosphate, sodium tripolyphosphate, and tetrasodium pyrophosphate are highly effective dispersants for preparation of fluid high solids slurries, they have a tendency to revert to orthophosphates, which are ineffective as dispersant. The reversion occurs under conditions of slightly elevated temperatures (over 25° C.) if the slurries are stored instead of being used immediately after preparation. This depolymerization of the polyphosphate produces instability in the dispersion, which is observable as an increase in the viscosity. Use of the organic dispersants, including naphthalene-sulfonate-formaldehyde condensates and polyacrylates, has been cited in the references mentioned above. These organic materials impart stability to the slurries whether used in conjunction with polyphosphates or used separately by themselves.

In addition, when latex containing alkaline soap is added to a slurry where a polyphosphate is the sole dispersant, the polyphosphates depolymerize, the clay absorbs some of the soap, and the viscosity of the coating color increases. The organic dispersants retain their efficiency and ensure constant viscosity of the coating color. Moreover, the polyacrylate salts are effective when only a small amount of the inorganic polyphosphate is replaced with it. Therefore, the polyacrylates function not only as excellent dispersants, but also act as protective colloids with a high affinity for the surfaces of the paper coating pigment. The properties of the final coated sheet are improved in such a way that coating colors with increasing amounts of polyacrylates behave as if more pigment binder were present.

This invention is directed to the use of oligomers as dispersants. Such oligomers have heretofore been known to be useful as conductive agents. The dispersants are essentially non-foaming, completely water soluble, anionic polyelectrolytes especially designed for dispersing solid particulate matter such as pigments, fillers, extenders, and other insoluble fine particles in aqueous systems. The resultant dispersions are very stable to heat. Furthermore, formulations containing reactive pigments such as zinc oxide or reactive additives like cationic biocides, especially mercury fungicides, have much improved stability.

The oligomers which are useful herein may be represented by the following formula:

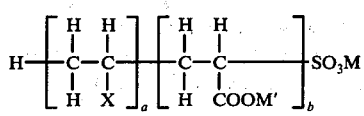

wherein M is a water soluble cation; X is selected from —CN and —COOCH$_3$; M' is a cation based on ammonia, an amine, or alkali metal such as lithium, sodium or potassium; $a+b$ is about 4 to 250; and $a/a+b$ is from about 0 to not greater than 0.6. In the preferred compounds M and M' are both sodium.

The invention comprises the use of the oligomers as dispersants for particulate matter in water, and as dispersants for the paper coating field in particular, as well as the new dispersion compositions obtained. The oligomers are useful in a range of 0.01 to 10 parts of oligomer, preferably 0.0125 to 5 parts of oligomer, and most preferably 0.02 to 3 parts of oligomer per 100 parts of particulate matter.

It is understood that the formula is not intended to depict the actual structure of the oligomers, because the structural units:

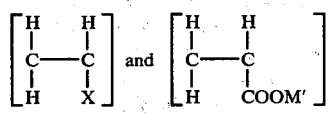

are randomly distributed throughout the molecule.

In the above generic formula the subscript "a" indicates the total moles of the X-group, on the average, per molecule, and "b" the total moles of —COOM', on the average, per molecule. The degree of polymerization, $a+b$, is broadly from about 4 to 250, and preferably from 10 to 60 as a general dispersant and 4 to 50 in the paper coating field. The mole fraction of the oligomer having the —X group as indicated by the ratio $a/a+b$ is broadly from about 0 to not greater than 0.6, preferably as a general dispersant 0.0 to 0.5, most preferably 0.0 to 0.40, while in the paper coating field preferably to 0 to 0.40, more preferably 0 to 0.20, and most preferably 0 to 0.10. When dispersing a pigment such as titanium dioxide, zinc oxide, calcium carbonate, clays and iron oxides, the $a/a+b$ ratio is preferably as low as possible, and most preferably is 0.

The oligomers of this invention are produced by the copolymerization of acrylic acid with acrylonitrile or methyl acrylate in water and in the presence of sodium bisulfite such that the amounts of each species correspond to the desired levels of $a$ and $b$ in the product. The oligomers so prepared are then neutralized with common bases, e.g., NaOH, KOH, NH$_3$, etc. Further details of the preparation of oligomers useful in this invention are in U.S. Pat. No. 3,646,099 of Leland E. Dannals incorporated by reference herein.

The oligomers have been found useful for the preparation of stable dispersions for a wide variety of pigments and particulate matter especially titanium dioxide, zinc oxide, calcium carbonate and kaolin. The resultant dispersions are themselves useful for compounding aqueous polymer emulsions, especially for formulations of water based coatings. The required amount of oligomer necessary to disperse a particular solid depends upon the nature, particle size, and amount of the solid, the exact oligomer used, and the overall formulation involved, but usually would be no more than 3% by weight based on the solid content, except for the most difficult composition. The usual treatment level is from about 0.01 to 10 parts by weight of oligomer dispersant per 100 parts of dry solids, and preferably 0.0125 to 5 parts, and most preferably 0.02 to 3 parts. Because of the high efficiency of dispersion with the oligomers herein fluidity can be achieved at very high solids levels with only a very small amount of the oligomer being required.

Furthermore, the oligomer may be used in conjunction with conventional polyphosphate dispersants so that an even lower level of oligomeric dispersant would be sufficient, preferably from about 0.005% to 2%, together with 0.5 to 7% of the polyphosphate to produce a dispersion with improved stability over a long term. The lowest and higher relative concentrations of the oligomer within the above concentration ranges do not necessarily result in the lowest possible viscosity. The minimum viscosity which can be attained, however, will generally be found within these concentration ranges.

The total solids of pigment which can be incorporated into the aqueous dispersion and still permit fluidity will also vary depending upon the particular composition and the fineness of the solid particles being dispersed. These solids may vary from about 25–85%, preferably from 30–85%, but will usually fall between 50 and 80%. The greater the amount of water, the lower the viscosity and the lower the amount of dispersant required.

While the pH of the resultant dispersions would ordinarily vary from neutral to moderately alkaline, e.g. about 7 to 11, the oligomers have been found to be effective dispersants over the broader pH range of 4.5 to 12. In addition, in those cases wherein the pH is customarily adjusted to afford an alkaline dispersion, the adjustment may be made with, for example, ammonia, sodium hydroxide, or sodium carbonate.

The oligomer is obtained as an aqueous solution as the reaction product from the polymerization. The reaction product may be used as an additive for dispersing the particulate matter without further purification or removal of traces of catalyst and monomer residues. The reaction solids during polymerization are not critical as far as the utility of the oligomers is concerned. In addition, the solids of the reaction product may be adjusted to any concentration to produce the solution of the oligomer which is used as the additive for preparation of dispersions. This concentrated solution of oligomer may contain any level of oligomer solids generally not exceeding 60%, but preferably between 15% and 30%, and may even be as low as 100 ppm, although this concentration does not affect the utility of the oligomer. The oligomer may also be recovered from the reaction mixture by any suitable means, such as spray drying, and used as a solid additive in place of the concentrated solution of oligomer. When a pigment dispersion is prepared, a dilute solution of oligomer may be made by dilution of the concentrated solution or dry oligomer with the solvent (water), to which the particulate matter is added. Alternatively, a paste of the solid matter and diluent (water) may be formed, and the concentrated solution or dry oligomer is then added to produce fluidity.

A wide variety of solid particulate matter may be dispersed using the oligomers. They include all common pigments and extenders or other materials commonly used as fillers, and may be combined with any organic or inorganic colored pigments as desired, and may be formulated with any of the usual additives which are employed in compoudning with pigments. The dispersions of the pigments with appropriate additives are used especially for compounding aqueous polymer emulsions, including those designed for water base coatings, especially for paint and paper coating. The pigments and extenders which may be dispersed to form a white pigment base to which additives including colored pigment would be added, may be any insoluble finely divided substance, for example, titanium dioxide, zinc oxide, calcium carbonate (whiting), clay such as china clay or kaolin, talc, silica, mica, barytes, etc. Colored pigments suitable herein include, for example, chrome yellow, molibdate orange, iron blue, chrome green, cadmium red or yellow, iron oxide red or yellow, chrome oxide green, ultramarine blue, mineral violet, cobalt blue, titanate yellow, as well as organic pigments like dichlorobenzidine yellows and oranges, hansa yellows, dinitroaniline orange, naphthols, toluidine red, lithol reds and rubines, BON reds and maroon, phthalocyamine blues and greens, quinacridones, isoindolinones, perylenes, etc. The dispersion of these pigments are useful for compounding emulsions for any application in which the compounded emulsions are used, but especially for applications in paints, paper coating, or other surface coatings, and adhesives which employ fillers. The powdered materials are mixed with a solution of dispersant in a solvent (water) in which they are insoluble. The ensuing paste may be ground in a mill as desired; however, a high shear mixer may be suitable for producing fluid dispersions. Various additives may be included in the dispersion. The most common additives for paints and for paper coating are preservatives and biocides including germicides, bactericides, and fungicides, thickeners, defoamers, coalescing solvents, plasticizers, and crosslinking agents.

The dispersion viscosity is measured with a Brookfield viscometer (RVT). In the evaluation, dispersion viscosity measured at 50 rpm in excess of 20,000 mPa.s (milli pascal seconds) is unacceptable; preferably the viscosity should be less than 10,000 mPa.s but is not expected to be less than 10 mPa.s. In a simple formulation of particulate matter, water, and dispersant at up to 75% solids, viscosity between 10 and 2,000 mPa.s is most preferable. For a formulation of paper coating clay, with pigment solids between 60% and 70%, the viscosity may range between 50 and 5,000 mPa.s. For a fully formulated paint pigment dispersion but without thickener, at 70% to 75% pigment solids, the viscosity may range between 100 and 10,000 mPa.s. Fluid dispersions can be prepared using oligomers within the scope of the invention; however, the resultant viscosities are more favorable within the preferred ranges of $a+b$ and $a/a+b$.

In order to illustrate more clearly the instant invention, attention is directed to the following examples:

EXAMPLE 1

A typical laboratory preparation and testing procedure for dispersion properties of an oligomer of the invention, wherein X is —CN, M and M' are both sodium, $a+b$ is 15.5, and $a/a+b$ is 0.35, as described:

The following materials are combined in a 1 liter resin flask.

| | |
|---|---|
| 280 ml | water |
| 16.4 g | Sodium bisulfite (9.2 phm, 0.088 moles) |
| 110 ml | (115.5 g) acrylic acid (65.1 phm, 0.094 moles) |
| 57 ml | (45.6 g) acrylonitrile (25.7 phm, 0.485 moles) |

The mixture under agitation is equilibrated in a water bath controlled at 30+ C., while nitrogen is allowed to flow through the reactor. Ammonium persulfate, 10% solution, is added incrementally from a burette using 0.25 ml aliquots every hour for 2 hours and again at 2½ hours, (a total of 1 ml is used) when no further exotherm is detected from the temperature of the reaction. The maximum temperature reached during polymerization is 33.6° C.

The Brookfield viscosity (RVT) of the solution is 600 mPa.s at 38.9% total solids. The solution is neutralized to pH 11.5 with 115.0 g of about 50% sodium hydroxide. The neutralized oligomer solution has a Brookfield viscosity of 330 mPa.s and total solids of 39.2%. A one gram portion of the reaction product is converted to its methyl ester in a boron trifluoride-methanol mixture, and the average molecular weight determined by vapor pressure to be 1150. A portion of about 200 ml of the reaction product is also diluted to a 25.0% wt. solution of oligomer to serve as a concentrated solution of dispersant.

The dispersing properties of the oligomer are evaluated by preparation of solid particulate matter dispersions as follows:

Weighed amounts of the solid particulate matter and water are mixed together using a spatula until a moist stiff paste is formed. The paste is then treated with increments of the concentrated solution of oligomer. After each addition, the paste is mixed for 1 minute using a laboratory mixer at high speed in attempts to disperse the solid matter. When sufficient dispersant has been added, a fluid dispersion is obtained under agitation. During the titration, fluidity is achieved suddenly with the addition of only a very small additional increment of dispersant. The Brookfield viscosity is measured when the dispersion first becomes fluid, and again every time after additional amounts of dispersant are added. The incremental addition is continued until a minimum viscosity is observed. The results of such fluidity titrations are given for the oligomer described above in Tables I and II, wherein titanium dioxide and zinc oxide are used as the solid matters, respectfully.

TABLE I

Dispersion of Titanium Dioxide with Oligomer of Example 1

| | |
|---|---|
| Formulation: 71.4% pigment solids: | 250 g titanium dioxide, rutile |
| | 100 g water |
| Concentrated Solution of Oligomer: | 25.0% wt. |
| Ratio[1] | Brookfield Viscosity (RVT), mPa.s 100 rpm, Spindle #3 |

TABLE I-continued

| | |
|---|---|
| 0.068 | >1000 |
| 0.079 | 825 |
| 0.090 | 584 |
| 0.102 | 479 |
| 0.113 | 393 |
| 0.124 | 309 |
| 0.136 | 317 |
| 0.147 | 336 |
| 0.181 | 430 |
| 0.226[2] | 466 |

[1]Parts of Oligomer/100 parts particulate matter. (This term has the same meaning throughout Tables I-IX).
[2]Final pigment solids - 71.0%

TABLE II

Dispersion of Zinc Oxide with Oligomer of Example 1

| Formulation: 71.4% pigment solids: | 250 g zinc oxide (coarse) |
| | 100 g water |
| Concentrated Solution of Oligomer: | 25.0% wt. |

| Ratio | Brookfield Viscosity (RVT), mpa.s 100 rpm, Spindle #3 |
|---|---|
| 0.068 | >1000 |
| 0.079 | 447 |
| 0.090 | 162 |
| 0.102 | 122 |
| 0.113 | 107 |
| 0.124 | 100 |
| 0.136 | 94 |
| 0.163 | 96 |
| 0.192 | 103 |
| 0.226[1] | 104 |

[1]Final pigment solids - 71.0%

EXAMPLE 2

The procedure of Example 1 is repeated to prepare an oligomer wherein X is —CN, M and M' are both sodium, $a+b$ is 20.9, and $a/a+b$ is 0.32.

The resultant oligomer is used as a dispersing agent for various particulate matter as shown in the fluidity titrations of Tables III–VI below.

TABLE III

Dispersion of Titanium Dioxide with Oligomer of Example 2

| Formulation: 75.0% pigment solids: | 225 g titanium dioxide, rutile |
| | 75 g water |
| Concentrated Solution of Oligomer: | 24.5% |

| Ratio | Brookfield Viscosity (RVT), mPa.s 100 rpm, Spindle #3 |
|---|---|
| 0.123 | >1000 |
| 0.148 | 954 |
| 0.172 | 610 |
| 0.197 | 606 |
| 0.222 | 682 |
| 0.246[1] | 863 |

[1]Final pigment solids - 74.5%

TABLE IV

Dispersion of Zinc Oxide with Oligomer of Example 2

| Formulation: 60.0% pigment solids: | 180 g zinc oxide 99.5% 325 mesh |
| | 120 g water |
| Concentrated Solution of Oligomer: | 24.5% |

| Ratio | Brookfield Viscosity (RVT), mPa.s 100 rpm, Spindle #3 |
|---|---|
| 0.123 | >1000 |
| 0.154 | 304 |
| 0.184 | 92 |
| 0.216 | 94 |
| 0.261 | 108 |
| 0.308 | 118 |
| 0.384 | 137 |
| 0.463 | 156 |
| 0.617 | 164 |
| 0.769[1] | 170 |

[1]Final pigment solids - 59.0%

TABLE V

Dispersion of Calcium Carbonate with Oligomer of Example 2

| Formulation: 75.0% pigment solids: | 225 g calcium carbonate. 92.9% 325 mesh |
| | 75 g water |
| Concentrated Solution of Oligomer: | 24.5% |

| Ratio | Brookfield Viscosity (RVT), mPa.s 100 rpm, Spindle #3 |
|---|---|
| 0.012 | >1000 |
| 0.025 | 756 |
| 0.037 | 449 |
| 0.049 | 362 |
| 0.061 | 342 |
| 0.086 | 318 |
| 0.123 | 302 |
| 0.172 | 312 |
| 0.233[1] | 339 |

[1]Final pigment solids - 74.5%

TABLE VI

Dispersion of No. 1 Coating Clay with Oligomer of Example 2

| Formulation: 61.0% pigment solids: | 350 g wet filter cake |
| Concentrated Solution of Oligomer: | 24.5% |

| | Brookfield Viscosity (RVT), mPa.s Spindle #3 | |
|---|---|---|
| Ratio | 100 rpm | 10 rpm |
| 0.299 | >1000 | — |
| 0.312 | 365 | 1250 |
| 0.325 | 173 | 420 |
| 0.338 | 128 | 200 |
| 0.351 | 98 | 140 |
| 0.364[1] | 102 | 130 |

| Formulation: 60.5% pigment solids: | 345 g dispersed clay containing 0.76 dispersant |
| | 208 g clay |
| | 136 g water |

| Dry Clay* Added | Ratio | Brookfield Viscosity (RVT), mPa.s Spindle #3 | |
|---|---|---|---|
| | | 100 rpm | 10 rpm |
| 0 | 0.364 | 102 | 130 |
| 20 | 0.368 | 128 | 210 |
| 40 | 0.395 | 139 | 310 |
| 60 | 0.418 | 198 | 520 |
| 80 | 0.444 | 296 | 720 |
| 100 | 0.488 | 443 | 1330 |
| 120[2] | 0.518 | >1000 | 2850 |

[1]Final pigment solids - 60.5%
[2]Final pigment solids - 70.2%
*Dry clay is added to raise the solids in the dispersion. After each addition, sufficient dispersant is also added to keep the viscosity at its minimum.

EXAMPLES 3–23

The basic procedure of Example 1 is repeated to prepare numerous oligomers within the scope of the invention. The oligomers are then tested for dispersant properties in normal commercial-type formulations containing water and ethylene glycol as coalescing solvent, the oligomer dispersant, a mercurial fungicide, and a defoamer. The dry pigment and extender are added to the aqueous solution of additives under slow mixing. The resulting paste is ground for 5 minutes with high speed mixing to produce the fluid dispersions. The Brookfield viscosity is then measured. Under high speed agitation, the dispersion is heated to 125° F., at which temperature it is maintained for 10 minutes if the dispersion remains fluids. The viscosity is then measured again. The composition of the tested oligomers are listed in Table VII and the results of the evaluations are compiled in Tables VIII and IX. The data demonstrate first that efficient dispersions are obtained for any $a+b$ throughout the range tested, next that only small amounts of dispersant are required to ensure fluidity, and finally that the dispersions remain stable to heat even in the presence of reactive fungicide.

TABLE VII
Composition of Oligomers: M,M' are Sodium. X is —CN

| Example | $a/a+b$ | $a+b$ | Concentration* A | (% Wt.) B |
|---|---|---|---|---|
| 3 | 0 | 13.9 | 32.8 | — |
| 4 | 0.17 | 20.1 | 46.1 | 25.0 |
| 5 | 0.26 | 34.5 | 46.0 | 24.8 |
| 6 | 0.31 | 50.6 | 38.7 | 24.6 |
| 7 | 0.32 | 20.9 | 38.7 | 25.6 |
| 8 | 0.35 | 15.5 | 39.2 | 25.0 |
| 9 | 0.35 | 30.4 | 38.9 | — |

*A = final concentration of reaction product after polymerization.
B = reaction product diluted with water to concentrations indicated.

TABLE VIII
Evaluation of Oligomers 3 through 9

Formulation: 250 g titanium dioxide, rutile ⎫
100 g talc ⎬ 70% pigment solids
126 g water + 24 g ethylene glycol ⎭
5 g 30% phenyl mercuric acetate
1 g Cofoam #2*

| Example | Polymer(1) Solution | Ratio(3) | Viscosity(2) Before Heating | After Heating |
|---|---|---|---|---|
| 10 | 3A | .93 | 1260 | 1140 |
| 11 | 4B | .85 | 620 | 340 |
| 12 | 5B | .89 | 680 | 420 |
| 13 | 6B | .84 | 940 | 420 |
| 14 | 7B | .88 | 690 | 410 |
| 15 | 8B | .89 | 680 | 420 |
| 16 | 9A | .88 | 670 | 380 |

*Cosan Chemical Company Trademark for proprietary defoamer.
(1)See Table VII
(2)Brookfield Viscosity (RVT), mPa.s, Spindle #3, 50 rpm ⎫ Same meaning in Table IX
(3)Parts oligomer per 100 parts of pigment at 68% pigment solids ⎭

TABLE IX
Evaluation of Oligomers 3 through 10

Formulation: 250 g titanium dioxide, rutile ⎫
200 g talc ⎬ 75% pigment solids
126 g water + 24 g ethylene glycol ⎭
5 g 30% phenyl mercuric acetate
1 g Cofoam #2

| Example | Polymer Solution | Ratio(1) | Viscosity Before Heating | After Heating |
|---|---|---|---|---|
| 17 | 3A | .73 | 11110 | 7230 |
| 18 | 4B | .50 | 5090 | 4940 |
|    | 4B | .67 | 4540 | 2640 |
| 19 | 5B | .49 | 4420 | 3620 |
|    | 5A | .71 | 4520 | 3280 |
| 20 | 6B | .55 | 6430 | 5130 |
|    | 6B | .65 | 5950 | 4080 |
| 21 | 7B | .57 | 7310 | 6010 |
|    | 7A | .69 | 5210 | 3490 |
| 22 | 8B | .56 | 9960 | 6480 |
|    | 8A | .70 | 6520 | 3580 |
| 23 | 9A | .61 | 6290 | 4200 |
|    | 9A | .69 | 7240 | 3610 |

(1)Parts of oligomer per 100 parts of pigment at 73% minimum pigment solids.

EXAMPLES 24-36

The effect of various oligomers within the scope of this invention on the surface tension of distilled water was determined. The results, as shown in Table X, prove that the oligomers useful as dispersants have no surface active properties. They have no effect in reducing the interfacial tension between water and air, i.e. they do not lower the surface tension of water. The seeming increases of surface tension values for the solutions containing the compounds of the invention are attributable to structural and viscosity phenomena.

A typical surfactant, the potassium salt of a compound having similar structure and composition with the exception of the terminal group being $—S—C_8H_{17}$ instead of $—SO_3Na$, shows a drastic reduction in the surface tension of water, and is listed in Table X below as "Comparison".

TABLE X
Surface Tension of Oligomers
X is —CN, M and M' are sodium, except Ex. 37

| Example | $\frac{a}{a+b}$ | $a+b$ | Concentration (% wt.) | dynes*/cm. |
|---|---|---|---|---|
| 24 | 0.35 | 15.5 | 24.9 | 77.3 |
| 25 | 0.18 | 33.6 | 25.0 | 78.7 |
| 26 | 0.31 | 50.6 | 24.6 | 76.9 |
| 27 | 0.17 | 20.2 | 24.8 | 69.0 |
| 28 | 0.26 | 34.5 | 24.8 | 77.7 |
| 29 | 0.35 | 30.4 | 24.9 | 76.9 |
| 30 | 0.32 | 20.9 | 0.1 | 73.0 |
| 31 | 0.32 | 20.9 | 0.5 | 73.2 |
| 32 | 0.32 | 20.9 | 2.6 | 72.8 |
| 33 | 0.32 | 20.9 | 4.8 | 72.0 |
| 34 | 0.32 | 20.9 | 24.5 | 76.2 |
| 35 | 0.45 | 31.3 | 24.5 | 74.6 |
| 36 | 0.42 | 21.2 | 24.7 | 73.7 |
| Comparison | 0.50 | 16.0 | 0.1 | 48.8 |

*Uncorrected, DuNouy Interfacial Tensiometer, ring circumference = 5.991 cm.
Surface tension, distilled water, room temperature, measured 71.8 dynes/cm.

EXAMPLE 37

The procedure of Example 1 is repeated to prepare an oligomer wherein M' and M are both sodium, X is $—CO_2CH_3$, $a+b$ is 15.8, $a/a+b$ is 0.35.

The resultant oligomer is used as a dispersing agent for the formulation previously described in TABLE IX, where Ratio of oligomer/100 parts particulate matter is 0.61, the viscosity (Brookfield (RVT), Spindle (#3, 50 rpm) before and after heating is 4550 mPa.s and 2810 mPa.s respectively.

EXAMPLE 38

This example shows the use of a dispersing agent of this invention.

The following pigment formulation is ball milled for 24 hours:
  42 parts water
  2 parts of the 25% solution of oligomer from Example 1
  55 parts zinc oxide, 99.5% through 325 mesh The resultant pigment slurry is next compounded in the following latex formulation:
  162 parts natural rubber latex, centrifuged to 62%
  2 parts 50% potassium hydroxide
  1-5 parts zinc oxide slurry from above The compounded latex is mixed thoroughly and then used as a dip for casting rubber films. The zinc oxide is customarily used in this composition to promote curing of the rubber film. In order to obtain a satisfactory cure, however, the zinc oxide must be predispersed so that any agglomerates of it are broken down to ultimate particle size.

After the rubber is cured, the films are checked to be certain that the physical properties of the rubber are satisfactory. Then, the films are stretched and placed under an optical microscope to determine if there is any agglomeration of the zinc oxide.

Samples containing 1, 2, 3, 4 and 5 parts, respectively, of the zinc oxide slurry are all found to have no evidence of pigment agglomeration.

If the oligomer is omitted from making the slurry, the zinc oxide does not slurry, and if it does not slurry, then it can not be added to the latex.

EXAMPLE 39

A typical test for illustrating the dispersing and stabilizing properties of the oligomer of Example 1 was as follows: To prepare a slurry of kaolin clay (Ultrawhite 90 - Englehard Minerals and Chemicals), 0.2% TSPP (tetrasodium pyrophosphate) is added to an undispersed filter cake of clay (60% solids) under low shear agitation. The solids are raised to 70% by adding clay which had been dried at 103° C. overnight and repulverized with a hammer mill. Sufficient TSPP is added to keep the concentration at 0.2% based on the dry weight of clay. This high solids composition is mixed under high shear agitation (sigma blade mixer) for 5 minutes. After the temperatures is allowed to come below 25° C., the Brookfield viscosity (RVT) is measured. In increments not greater than 0.05% TSPP, additional TSPP is added. After each addition, the slurry is ground, allowed to cool, and the viscosity is observed. Additions are repeated until a minimum viscosity is obtained. In this example 0.375% TSPP is found to give the minimum viscosity at 70.0% clay solids. To the final optimized slurry the organic dispersant is added and mixed thoroughly, followed by addition of 0.05% of the germicide 3,5-dimethyltetrahydro-1,3,5-2H-thiadiazine-2-thione (Metasol D3TA, Merck Chemical). The initial reading of pH, solids, and viscosity are recorded and samples are placed in a shaker bath preset at 45° C. Subsequently, samples are removed from the bath, allow to cool to 25° C., readings of pH, solids, and viscosity are recorded, and the samples are returned to the bath. The observations are made at intervals for 30 days. The results when oligomer of Example 1 is used are given in TABLE XI.

TABLE XI

Stabilization of Clay Slurries, Aged at 110° F
0.370% TSPP
0.05% Metasol D3TA
Brookfield Viscosities (RVT) and Clay Solids

| Organic Dispersant | | Time 0 | 1 wk | 2 wk | 3 wk | 4 wk |
|---|---|---|---|---|---|---|
| none | 100rpm | 464 | 1218 | 2180 | 3510 | 4870 |
|  | 10rpm | 1110 | 5500 | 12640 | 20100 | 25000 |
|  | Solids | 69.8 | 69.5 | 69.7 | 69.6 | 70.0 |
|  | pH | 6.5 | 6.0 | 5.8 | 5.8 | 5.8 |
| Oligomer of Ex. 1 at 0.01% | 100rpm | 555 | 635 | 772 | 912 | 912 |
|  | 10rpm | 1690 | 1890 | 2290 | 2800 | 2880 |
|  | Solids | 69.8 | 70.0 | 69.3 | 70.0 | 69.0 |
|  | pH | 6.5 | 6.0 | 5.8 | 5.8 | 5.8 |
| Oligomer of Ex. 1 | 100rpm | 730 | 728 | 593 | 532 | 581 |
|  | 10rpm | 3330 | 2800 | 1850 | 1480 | 1630 |

TABLE XI-continued

Stabilization of Clay Slurries, Aged at 110° F
0.370% TSPP
0.05% Metasol D3TA
Brookfield Viscosities (RVT) and Clay Solids

| Organic Dispersant | | Time 0 | 1 wk | 2 wk | 3 wk | 4 wk |
|---|---|---|---|---|---|---|
| at 0.02% | Solids | 69.5 | 69.9 | 69.6 | 69.5 | 69.7 |
|  | pH | 6.5 | 6.0 | 5.8 | 5.8 | 5.8 |
| Oligomer of Ex.1 at 0.015% | 100rpm | 500 | 495 | 606 | 664 | 838 |
|  | 10rpm | 1950 | 1950 | 2430 | 2450 | 2360 |
|  | Solids | 72.4 | 71.8 | 72.1 | 72.6 | 73.0 |
|  | pH | 6.4 | 6.0 | 5.9 | 5.9 | 5.8 |
| Oligomer of Ex. 1 at 0.024% | 100rpm | 695 | 425 | 545 | 662 | 954 |
|  | 10rpm | 3010 | 1420 | 1770 | 2000 | 2340 |
|  | Solids | 72.4 | 71.8 | 72.0 | 72.7 | 72.6 |
|  | pH | 6.4 | 6.0 | 5.9 | 5.9 | 5.8 |
| Oligomer of Ex. 1 at 0.034% | 100rpm | 465 | 354 | 470 | 546 | 728 |
|  | 10rpm | 1440 | 1040 | 1480 | 1710 | 1980 |
|  | Solids | 72.5 | 72.2 | 71.8 | 72.5 | 72.6 |
|  | pH | 6.4 | 6.0 | 5.9 | 5.9 | 5.8 |

EXAMPLE 40

To prepare a coating color containing the Oligomer of Example 1, the following procedure is followed: 250 g of Ultrawhite 90 (dry clay), 97 g water, 1.26 g TSPP decahydrate, and 1 g 25% solution of oligomer of Example 1 are combined and mixed for 10 minutes in a sigma blade mixer. At the end of the mixing 10 g additional water is added to dilute the slurry to 70% clay solids. The coating color is prepared by combining 300 g of the 70% clay slurry and 147 g 20% starch (5# Penford Gum 390, precooked at 90° C. for 20 minutes). The coating color is thinned by diluting to 40% with water and is applied to uncoated paper with a #5 wound wire applicator and dried. The final coating sheet so far obtained can be further mechanically processed, for example, by calendering to produce a high gloss coated paper. The paper exhibited excellent properties with respect to brightness, opacity, gloss, surface strength, ink absorbancy, and smoothness.

EXAMPLE 41-45

The basic procedure of Examples 1 was repeated to prepare additional oligomers within the scope of the invention wherein $a/a+b = 0$. The oligomers were then tested for dispersant properties according to the procedure described in Example 39. In addition the oligomer of Example 3A was also tested in the formulation of Example 39. The composition of the tested oligomers are listed in TABLE XII and the results of the evaluations are compiled in TABLE XIII.

TABLE XII

Composition of oligomers: M,M' are all sodium
$a/(a+b) = 0$

| Example | a + b | Concentration* (% wt.) A | B |
|---|---|---|---|
| 41 | 5.8 | 47.3% | — |
| 42 | 6.6 | 36.1% | 25.1% |
| 43 | 8.2 | 46.9% | — |
| 44 | 56.4 | 35.7 | — |

* See TABLE VII

TABLE XIII

Stabilization of Clay Slurries, Aged at 110° F.
0.35% TSPP
0.05% Metasol D3TA
Brookfield Viscosity (RVT) and Clay Solids

| Oligomer Solution | Time pH | 0 6.5 | 1 week 6.0 | 2 weeks 5.8 | 3 weeks 5.8 | 4 weeks 5.8 |
|---|---|---|---|---|---|---|
| 41A at 0.031% | 100 rpm | 370 | 370 | 440 | 400 | 400 |
|  | 10 rpm | 1070 | 930 | 1060 | 960 | 1040 |
|  | Solids | 70.7 | 70.7 | 70.4 | 70.6 | 70.7 |
| 43A at 0.032% | 100 rpm | 330 | 430 | 370 | 420 | 380 |
|  | 10 rpm | 940 | 1060 | 910 | 1010 | 940 |

TABLE XIII-continued

Stabilization of Clay Slurries, Aged at 110° F.
0.35% TSPP
0.05% Metasol D3TA

| Oligomer Solution | | Time<br>pH | 0<br>6.5 | 1 week<br>6.0 | Brookfield Viscosity (RVT)<br>and Clay Solids<br>2 weeks<br>5.8 | 3 weeks<br>5.8 | 4 weeks<br>5.8 |
|---|---|---|---|---|---|---|---|
| 3A<br>at 0.027% | | Solids<br>100 rpm<br>10 rpm<br>Solids | 71.0<br>567<br>1650<br>70.0 | 70.9<br>547<br>1590<br>70.4 | 70.2<br>516<br>1440<br>70.4 | 70.7<br>481<br>1300<br>70.4 | 70.5<br>496<br>1390<br>70.5 |

EXAMPLES 45 & 46

The dispersing properties of the oligomers of Examples 42 and 44 were evaluated further by preparation of dispersions of solid particulate matter according to the procedure described in Example above. The results of the fluidity titrations are shown in TABLES XIV–XV

TABLE XIV

Dispersion of Titanium Dioxide with Oligomer of Example 42.

Formulation: 71.4% Pigment Solids: 250 g titanium dioxide rutile
100 g water
Concentrated Solution of Oligomer: 42B, 25.1% Solids

| Ratio | Brookfield Viscosity (RVT)<br>100 rpm, Spindle #3, mPa, s |
|---|---|
| 0.067 | 796 |
| 0.071 | 486 |
| 0.075 | 347 |
| 0.080 | 251 |
| 0.085 | 226 |
| 0.095 | 188 |
| 0.111 | 186 |
| 0.124 | 188 |
| 0.148 | 212 |
| 0.200[1] | 259 |

[1]Final pigment solids - 71.0%

TABLE XV

Dispersion of Zinc Oxide with Oligomer of Example 44

TABLE XV-continued

Formulation: 71.4% Pigment Solids: 250 g zinc oxide (coarse)
100 g water
Concentrated solution of Oligomer: 44A, 35.7% Solids

| Ratio | Brookfield Viscosity (RVT)<br>100 rpm, Spindle #3, mPa.s |
|---|---|
| 0.069 | 1000 |
| 0.082 | 683 |
| 0.102 | 283 |
| 0.130 | 180 |
| 0.186[1] | 125 |

[1]Final pigment solids - 71.0%

What is claimed is:

1. A dispersing agent for solid particulate matter in an aqueous system consisting of an oligomer having the general formula

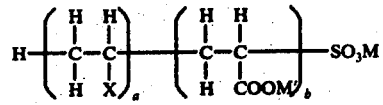

wherein M is a sodium cation; X is selected from the group consisting of —CN and —COOCH$_3$; M' is a sodium cation; $a + b$ is about 4 to about 250 and $a/a+b$ is 0.0.

2. The dispersing agent of claim 1 wherein $a+b$ is 4 to 50.

* * * * *